United States Patent
Singh et al.

(10) Patent No.: US 11,864,932 B2
(45) Date of Patent: Jan. 9, 2024

(54) X-RAY IMAGING SYSTEMS FOR REDUCING ARTEFACTS ASSOCIATED WITH ANTI-SCATTER GRIDS AND METHODS OF OPERATING THE SAME

(71) Applicant: KONINKLIJKE PHILIPS N.V., Eindhoven (NL)

(72) Inventors: Nishant Singh, Son en Breugel (NL); Klaus Jürgen Engel, Veldhoven (NL); Johannes Wilhelmus Maria Jacobs, Boxtel (NL); Bernd Menser, Hauset (BE); Lester Donald Miller, Hudson, OH (US); Fred Simon Berend Van Nijnatten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/797,294

(22) PCT Filed: Dec. 8, 2021

(86) PCT No.: PCT/EP2021/084690
§ 371 (c)(1),
(2) Date: Aug. 3, 2022

(87) PCT Pub. No.: WO2022/128654
PCT Pub. Date: Jun. 23, 2022

(65) Prior Publication Data
US 2023/0200756 A1    Jun. 29, 2023

(30) Foreign Application Priority Data
Dec. 14, 2020   (EP) .................................... 20213697

(51) Int. Cl.
*A61B 6/03* (2006.01)
*A61B 6/00* (2006.01)

(52) U.S. Cl.
CPC ............ *A61B 6/032* (2013.01); *A61B 6/4007* (2013.01)

(58) Field of Classification Search
CPC ..... A61B 6/032; A61B 6/4007; A61B 6/4291; A61B 6/5282
See application file for complete search history.

(56) References Cited

U.S. PATENT DOCUMENTS 10,861,155 B2    12/2020   Bernhardt
2006/0188146 A1   8/2006   Behiels
(Continued)

FOREIGN PATENT DOCUMENTS

CN    110974275 A    4/2020
EP    0962888 A2     8/1999
(Continued)

OTHER PUBLICATIONS

PCT International Search Report, International application No. PCT/EP2021/084690, dated Feb. 28, 2022.
(Continued)

*Primary Examiner* — Courtney D Thomas
(74) *Attorney, Agent, or Firm* — Larry Liberchuk

(57) ABSTRACT

The disclosure relates to an X-ray imaging system for acquiring two-dimensional or three-dimensional images of a subject. A relative position of an X-ray emitting region, as seen in a coordinate system which is stationary relative to an anti-scatter arrangement and/or an X-ray sensitive surface is controlled so that a first and a second image are acquired at different relative positions of the X-ray emitting region relative to the anti-scatter arrangement and/or the X-ray sensitive surface (10). A data processing system of the imaging system generates an output image, based on each of the images. In the output image, artefacts generated by the (Continued)

anti-scatter arrangement, are reduced, suppressed or eliminated compared to the first and the second image.

16 Claims, 12 Drawing Sheets

(56) References Cited

U.S. PATENT DOCUMENTS

| | | |
|---|---|---|
| 2012/0183124 A1 | 7/2012 | Kaneko |
| 2016/0258885 A1 | 9/2016 | Rothe |
| 2019/0059846 A1 | 2/2019 | Jiang |
| 2020/0258222 A1* | 8/2020 | Bernhardt ............ A61B 6/4441 |

FOREIGN PATENT DOCUMENTS

| | | |
|---|---|---|
| WO | WO2012106204 A1 | 8/2012 |
| WO | WO2015010913 A1 | 1/2015 |
| WO | WO2018194937 A1 | 10/2018 |

OTHER PUBLICATIONS

Alexeev T. et al., "Novel Ring Artifact Suppression in CBCT with 2D Anti Scatter Grids", Medical Physics, vol. 46, No. 5, pp. 2181-2193, May 2019.

Cobos S.F. et al., "Reduction of Ring Artifacts Caused by 2D Anti-Scatter Grids in Flat-Panel CBCT", Proceedings of SPIE MI 2020, vol. 11312, Medical Imaging 2020: Physics of Medical Imaging; 1131228-1-1131228-7, 2020.

Yu Z. et al., "Simultaneous Scatter Rejection and Correction Method Using 2D Anti-Scatter Grids for CBCT", Proceedings of SPIE—the International Society of Optical Engineering, pp. 1-16, Feb. 2020.

Van Der Maas, R.J.R. et al., "Advanced Geometric Calibration and Control for Medical X-Ray Systems", TU/e, Eindhoven University of Technology, Mar. 3, 2016.

Alexeev T. et al., "A Novel Total Variation Based Ring Artifact Suppression Method for CBCT Imaging with Two-Dimensional Antiscatter Grids", Medical Physics, vol. 46, No. 5, pp. 2181-2193, May 2019.

Rana R. et al., "Scatter Estimation and Removal of Anti-Scatter Grid-Line Artifacts from Anthropomorphic Head Phantom Images Taken with a High Resolution Image Detector for CBCT", Medical Imaging 2016: Physics of Medical Imaging, Proceedings of SPIE, vol. 9783, pp. 978364-1-978364-10, 2016.

Kim K. et al., "A Grid-Line Suppression Technique Based on Deep Convolutional Neural Networks", Proceedings of SPIE Medical Imaging 2020: Image Processing, vol. 11313, pp. 1131327-1-1131327-8, Mar. 2020.

Zhou S. et al., "Multi-View Image Denoising Using Conventional Neural Network", Sensors, vol. 19, No. 11, 2597, 2019.

Mutto C.D et al., "Scene Segmentation Assisted by Stereo Vision", 2011 International Conference on 3D Imaging, Modeling, Processing, Visualization and Transmission, pp. 57-64.

Wang L. et al., "Stereoscopic Inpainting: Joint Color and Depth Completion from Stereo Images", 2008 IEEE Conference on Computer Vision and Pattern Recognition, Anchorage, AK, pp. 1-8, 2008.

Maslowski A. et al., "Acuros CTS: A Fast, Linear Boltzmann Transport Equation Solver for Computed Tomography Scatter—Part I: Core Algorithms and Validation", Medical Physics, vol. 45, No. 5. pp. 1899-1913, May 2018.

* cited by examiner

X-RAY IMAGING SYSTEMS FOR REDUCING ARTEFACTS ASSOCIATED WITH ANTI-SCATTER GRIDS AND METHODS OF OPERATING THE SAME

FIELD OF THE INVENTION

The present invention relates to X-ray imaging systems for generating medical images and methods for operating the same. Specifically, the present invention relates to X-ray imaging systems, which reduce, suppress or eliminate artefacts associated with anti-scatter grids.

BACKGROUND OF THE INVENTION

In X-ray medical imaging, anti-scatter grids are a well known technology used to prevent degradation of image quality caused by X-ray beams, which are scattered at the patient. As X-rays interact with tissue, the X-rays become attenuated, as well as scattered by the tissue. X-rays propagating in a direct line from the X-ray source to the detector system are desired. On the other hand, contrast and signal-to-noise ratio of image details are reduced by scatter.

Typically, anti-scatter grids include a regular array of cells, which are separated by radiopaque septa. The grid is placed between the patient and the detector during the exposure so that desirable electromagnetic radiation can pass through the grid, while undesirable electromagnetic radiation, which is caused by scattering within the tissue, is eliminated or suppressed by absorption within the septa walls.

The most common anti-scatter grids are one-dimensional grids (i.e. linear grids) meaning that the projection of the lamellae walls on the X-ray sensitive surface of the detector system are lines. Such anti-scatter grids are typically made of strips of X-ray-opaque lamellae, which are sandwiched between more X-ray transparent spacer materials. For more efficient scatter reduction, the grid walls preferably should be two-dimensional, i.e. the projection of the lamellae walls onto the X-ray sensitive surface of the detector are not lines but forms a two-dimensional pattern. Such two-dimensional grid walls allow elimination of scatter from all directions.

Since the lamellae are walls of the anti-scatter grids are comparatively nontransparent for the X-rays generated by the X-ray source, the anti-scatter grid casts a shadow of the X-ray radiation on the X-ray sensitive surface of the detector system. These shadows are undesirable, since they can obstruct the image and make clinical evaluation of the images more difficult or even impossible. This has led to the development of filters, which reduce artefacts in the X-ray images associated with the anti-scatter grids. However, it has been shown that the variety of different technical physical processes, which contribute to the artefacts makes it difficult to eliminate the artefacts in the X-ray images in a satisfactory manner Therefore, there is a need for providing improved X-ray imaging systems and methods, which use anti-scatter grids.

SUMMARY OF THE INVENTION

Embodiments of the present disclosure pertain to an X-ray imaging system for acquiring two-dimensional or three-dimensional images of a subject. The imaging system includes an X-ray source configured to emit X-rays from one or more X-ray emitting regions; a detector system configured to receive a portion of the X-rays, which has been passed through the subject, wherein the X-rays are received on an X-ray sensitive surface of the detector system; and an anti-scatter arrangement, which is arranged in the beam path of the X-rays between the X-ray emitting region and the detector system, in particular between the subject and the detector system. The imaging system is configured to acquire a first and a second image of the subject, wherein each of the first and second images shows (a) a same portion of a body of the subject and (b) an image artifact generated by the anti-scatter arrangement. The imaging system is configured to: control a relative position of at least one of the one or more X-ray emitting regions, as seen in a coordinate system which is stationary relative to the anti-scatter arrangement and/or the X-ray sensitive surface so that the first and second images are acquired at different relative positions of the at least one X-ray emitting region relative to the anti-scatter arrangement and/or the X-ray sensitive surface. The data processing system is further configured to generate, using a data processing system of the imaging system, an output image, based on each of the first and second images. The output image shows the portion of the body and in the output image, artefacts generated by the anti-scatter arrangement, are reduced, suppressed or eliminated compared to the first and the second image.

The X-ray imaging system may include an X-ray projection imaging system, an X-ray computed tomography system, and/or an X-ray tomosynthesis system.

The X-ray computer tomography system may be configured as a cone beam computed tomography system, i.e. the X-rays which are emitted from the X-ray source are divergent, forming a cone. Additionally or alternatively, the X-ray computed tomography system may be configured as a fan beam computed tomography system. The computed tomography system may be a single-slice scanner or a multi-slice scanner.

The two-dimensional images, which are generated by the imaging system may be projection radiography images. The three-dimensional images, which are generated by the imaging system may be reconstructed images based on two-dimensional X-ray projection images. The reconstructed images may be generated by a computed tomography system.

If the imaging system is configured as a computed tomography system, the first and second images may be acquired during a rotational movement of the X-ray source and the detector system about a body portion of the subject. The rotational movement may keep the relative position of the X-ray source relative to the anti-scatter arrangement and/or the X-ray sensitive surface invariant. Therefore, the first and the second images may show the body portion from different imaging projection axes.

The X-ray source may be configured as an X-ray tube. The X-ray source may be configured to generate one or more electron beams, which impinge on an anode. The anode may be configured as a rotary anode. The one or more X-ray emitting regions together may substantially form or may form a point source. Each of the X-ray emitting regions may be formed by a focal spot generated on a target of the X-ray source. The target may be an anode, in particular a rotating anode. The one or more X-ray emitting regions may represent a source size of less than 100 micrometers, or less than 1,000 micrometers. The source size may be defined as a maximum distance of two points, each of which being located within at least one of the X-ray emitting regions. The X-ray source may include an electron-optical system, which is configured for generating one or more electron beams, which impinge on a target of the X-ray source. The target may be an anode, in particular a rotary anode. A spectrum of the X-rays may have a cut-off energy, which is greater than 2 keV or greater than 20 keV. The cut-off energy may be lower than 10 MeV or lower than 150 kV. The cut-off energy may correspond to an acceleration voltage setting of the X-ray source. The acceleration voltage may accelerate electrons of one or more electron beams generated by the X-ray source, which impinge on an anode of the x-ray source.

The X-ray sensitive surface of the detector system may be flat or curved in one or two dimensions. In embodiments, in which the X-ray sensitive surface is curved, a center of curvature of the X-ray sensitive surface may be located or substantially located at a position of the X-ray emitting regions.

The detector system may be configured as an image recording device. The X-ray sensitive surface may include or may be formed by a plurality of pixels. The pixels may may be arranged in a two-dimensional array. Size of the X-ray sensitive surface portion formed by one of the pixels may be smaller than 200 micrometers or smaller than 1 millimeter. The size may be may be larger than 20 micrometers, or larger than 90 micrometers.

The anti-scatter arrangement may include a linear anti-scatter grid (also denoted as one-dimensional anti-scatter grid) and/or a two-dimensional anti-scatter grid. The term "one-dimensional anti-scatter grid" may be defined to mean that a projection of the anti-scatter grid onto the X-ray sensitive surface represent or substantially represent lines or a comb-like structure. The term two-dimensional anti-scatter grid may be defined to mean that a projection of the anti-scatter grid onto the X-ray sensitive surface represent a two-dimensional pattern, in particular a two-dimensional square grid pattern.

The anti-scatter grid may include a plurality of grid septa, which separate a plurality of cells of the anti-scatter grid from each other. The septa may be arranged in parallel or substantially parallel walls to form the one-dimensional anti-scatter grid. The two-dimensional anti-scatter grid may include septa, which form a crossed-grid structure.

An aspect ratio of at least a portion of the septa may be greater than 2 or greater than 8. The aspect ratio may be smaller than 40, or smaller than 16.

The septa may be made of or may include metal, in particular metal as a main constituent. By way of example, the septa may contain or may include as a main constituent one or a combination of: tungsten (W), lead (Pb) or tantalum (Ta).

The septa of the one-dimensional or two-dimensional anti-scatter grid may form a plurality of cells, each of which having an X-ray transmittance which is greater than or may be at least 5 times or at least 10 times or at least 20 times the X-ray transmittance of each of the septa. The cells may be at least partially filled with air or may at least partially filled with a filler material. Examples for filler materials, which can be used for the cells are plastics, such as polymeric compounds or paper, such as carbon paper. The filler material may be configured to increase the mechanical rigidity and positional accuracy of the anti-scatter arrangement.

The anti-scatter arrangement may be focused or unfocused. The focused anti-scatter arrangement may be configured to improve the contrast of the acquired images. The focused one-dimensional anti-scatter grid may include septa which form grid cells, wherein each of the grid cells points to an axis which extends or substantially extends through the one or more X-ray emitting regions.

The data processing system may include a computer system having a processor and a memory for storing instructions processable by the processor. The processor may execute an operating system. The data analysis system may further include a user interface configured to allow a user to receive data from the data processing system and/or to provide data to the data processing system. The user interface may include a graphical user interface.

The artefacts, which are associated with the anti-scatter arrangement may include our shadow structure, which corresponds to a projected shape of the septa of the anti-scatter grid, calculated by a central projection with the one or more X-ray emitting regions being the center of protection.

Each of the first and second image may be a grayscale image. Each of the pixel values may be indicative or substantially indicative of an intensity of detected X-ray radiation.

The reduction, suppression or elimination of the artefacts generated by the anti-scatter arrangement may be a reduction, suppression or elimination of a contribution of an image artefact generated by the anti-scatter arrangement to the pixel data values of the image. In other words, in the output image, the pixel data values represent or substantially represent pixel data values of an image, which has been required without the anti-scatter arrangement.

According to an embodiment, the data processing system is configured to use an algorithm, which uses differences between the first and the second images, which are caused by the different relative positions of the at least one X-ray emitting region to obtain the reduction, suppression, or elimination of the artefacts associated with the anti-scatter arrangement.

In other words, the algorithm may be sensitive to the difference between the first and the second image. The first image may be different from the second image. The difference between the first and the second image may be at least partially caused by the different relative positions of the one or more X-ray emitting regions relative to the anti-scatter arrangement and/or relative to the X-ray sensitive surface. The algorithm may be configured to read at least a portion of the first image and at least a portion of the second image and to output data representative of the output image. At least a portion of the output image may correspond to at least a portion of the field of view of the first image and to at least a portion of the field of view of the second image.

According to an embodiment, the data processing system is configured to generate the output image using a machine learning based algorithm The machine learning based algorithm may generate the output image based on data of, or derived from, the first image and the second image. Deriving the data from the first and from the second image may include determining a region in the first image region and a region in the second image region so that the image regions are corresponding image regions. The corresponding image regions may show or substantially show the same body portion. Additionally or alternatively, the deriving of the data from the first and from the second image may include applying one or more filters to the first and second images.

The term "machine learning based algorithm" may be defined to mean that the algorithm was generated using machine learning. The machine learning based algorithm, which is used to generate the output image may be in a trained state. The machine learning process may have been performed using a data processing system different than the data processing system of the imaging system. Alternatively, the data processing system of the imaging system may be configured for machine learning.

According to a further embodiment, the machine learning based algorithm includes an artificial neural network (ANN).

The artificial neural network may include an input layer, one or more intermediate layers and an output layer. The artificial neural network may be configured as a convolutional neural network.

An image, which is outputted by the output layer may correspond or substantially correspond to at least a portion of the output image. Alternatively, the image which is output by the output layer of the ANN may be processed by the data processing system using further algorithms, such as filters.

According to a further embodiment, the ANN has at least two image input channels. The data processing system may be configured to use a first one of the image input channels for data of, or derived from at least a portion of the first image. Additionally, the data processing system may be configured to use a second one of the image input channels for data of or derived from at least a portion of the second image.

Each of the input channels may process one of the input images without processing the other one of the input images. Each of the input channels may generate a channel output image. The ANN may be configured to combine the channel output images. Combining the channel output images may include forming a pixel-wise sum and/or a pixel-wise weighted sum of pixel data values of the channel output images. Additionally or alternatively, other combining operations are conceivable, such as one or a combination of: pixel-wise multiplication, pixel-wise subtraction and pixel-wise division. Further examples for combining operations are described in the article "Multi-View Image Denoising Using Conventional Neural Network", written by Shiwei Zhou et al. and published in Sensors, 19, 2597 (2019). The contents of this document is incorporated by reference for all purposes. Specifically, the architecture described in connection with FIG. 1 of this article provides an example for a combining operation.

After combination of the channel output images, the ANN may further process the combined image using a further artificial neural network, which receives the combined image as input. The further artificial neural network may be configured as a convolutional neural network. Additionally or alternatively, the combined image may be processed using one or more non-artificial neural network algorithms. Further, it is also conceivable that the combined image represent the output image of the ANN.

At least one or both of the input channels may include a residual neural network. The term "residual neural network" may be defined to mean a neural network, which includes one or more residual connections. A residual connection may be defined as a shortcut which skips one or more layers. By way of example, a residual connection may be configured to skip a group of two or three layers.

According to an embodiment, the generation of the output image includes: determining, using the data processing system, a plurality of image regions of the first image and a plurality of image regions of the second image, which substantially correspond to the image regions of the first image so that a plurality of pairs of corresponding or substantially corresponding image regions are obtained. The generation of the output image may further include sequentially processing the pairs, using the data processing system, to generate, for each of the pairs, a corresponding region of the output image. For each of the pairs of corresponding or substantially corresponding image regions, each of the images of the respective pair may show or substantially show the same body portion of the subject.

The image regions of the first and second image may be of equal or substantially equal size. Each of the image regions may have a square or rectangular shape. Each of the image regions may be a non-divided image region. The data processing system may be configured to combine output images, which correspond to different image portions, to form a combined image. The field of view of the combined image may substantially correspond to the sum of the field of views of the individual output images.

According to an embodiment, a distance between the different relative positions is at least 50 micrometers or at least 100 micrometers, or at least 400 micrometers or at least 800 micrometers, or at least 1,000 micrometers, or at least 5,000 micrometers. The distance may be measured as a distance between centers of the X-ray emitting regions, or as the distance between the focal spots, which form the X-ray emitting regions. The distance may be less than 10 millimeters or less than 5 millimeters, or less than 1 millimeter.

According to a further embodiment, the anti-scatter arrangement includes a one-dimensional or two-dimensional array of cells, which are separated from each other by septa. An X-ray transmittance of each of the cells is greater than an X-ray transmittance of the septa.

According to a further embodiment, the X-ray source includes a housing which houses an electron optical system for generating an election beam and a target for receiving the electron beam so that the X ray emitting region is arranged within the housing. The imaging system may be configured to control the X-ray source to controllably displace the at least one X-ray emitting region within the housing.

The housing may have a housing wall, which is configured to shield X-rays. The housing may also include an X-ray transmissive window through which the X-rays exit from the housing in a direction toward the anti-scatter arrangement and X-ray sensitive surface.

According to a further embodiment, the electron optical system is configured to selectively deflect the electron beam so that an impingement location of the electron beam on the target is changed. The control of the relative position of the at least one X-ray emitting region may include varying the impingement location on the target using the electron optical system.

Additionally or alternatively, the X-ray source is configured to generate a first electron beam generating a first X-ray emitting region and a second electron beam generating a second X-ray emitting region. The control of the relative position of the at least one or more X-ray emitting regions may comprise actuating and deactivating the two electron beams so that the electron beams are sequentially activated.

By way of example, the beams may be sequentially in an activating state so that the X-ray source alternatingly switches between the first X-ray emitting region and the second X-ray emitting region. The switching between the first and second X-ray emitting regions may change the relative position of the X-ray emitting region relative to the anti-scatter arrangement and/or relative to the X-ray sensitive surface.

The target may be an anode, in particular a rotary anode. The deflection of the electron beam may be at least partially generated by electrostatic and/or magnetic deflection, for example by using electrodes and/or coils. Additionally or alternatively, the X-ray source may be configured to displace the target within the housing so that the X-ray emitting region is displaced within the housing.

According to a further embodiment, the imaging system includes an actuator, which is in operational communication with at least a portion of the anti-scatter arrangement and/or with at least a portion of the detector system. The imaging system may be configured so that the variation of the position of the at least one X-ray emitting region relative to the anti-scatter arrangement (9) and/or relative to the X-ray sensitive surface includes controlling the actuator.

The X-ray imaging system may be configured so that the controllable actuation of the actuator varies an angle of a major plane of the anti-scatter arrangement relative to the X-ray sensitive surface. The variation of the angle may be larger than 0.01 degrees or larger than 0.02 degrees, or larger than 0.03 degrees. The variation may be smaller than 10 degrees or smaller than 5 degrees or smaller than 1.5 degrees or smaller than 0.5 degrees.

The actuator may be may include one or more piezoelectric elements. However, other configurations of the actuator may be conceivable, such as electrostatic and/or electromagnetic switching members. The actuator may be configured to change a position and/or an orientation of the anti-scatter arrangement relative to the X-ray sensitive surface. Additionally or alternatively, the actuator may vary a position and/or orientation of the anti-scatter arrangement and the X-ray sensitive surface. The position and/or orientation may be varied relative to a support structure, which supports the X-ray sensitive surface and the anti-scatter arrangement.

A displacement range of the actuator may be at least 0.1 millimeters or at least 0.3 millimeters.

According to a further embodiment, the imaging system is further configured to acquire the first and the second image within a time period of less than 20 milliseconds, or less than 200 microseconds.

According to a further embodiment, the imaging system includes a measurement unit which is configured to acquire position data indicate of a position of one or more of the X-ray emitting regions.

According to a further embodiment, the data processing system is configured to determine the output image further based on the position data.

Embodiments of the present disclosure further pertain to a method for operating an X-ray imaging system for acquiring two-dimensional or three-dimensional images of a subject and for reducing artefacts which are generated by an anti-scatter arrangement of the X-ray imaging system. The X-ray imaging system includes: an X-ray source configured to emit X-rays from an one or more X-ray emitting regions; and a detector system configured to receive a portion of the emitted X-rays, which have been passed through the subject on an X-ray sensitive surface (10) of the detector system. The anti-scatter arrangement is arranged in the beam path of the X-rays between the subject and the detector system. The method includes: acquiring a first and a second image of the subject so that each of the first and second images shows at least (a) a same portion of a body of the subject; and (b) an artifact generated by the anti-scatter arrangement. The method further includes controlling a relative position of at least one of the X-ray emitting regions relative to the anti-scatter arrangement and/or the X-ray sensitive surface so that the first and second images are acquired at different relative positions of the at least one X-ray emitting region. The method further includes generating, using a data processing system of the imaging system, an output image, based on each of the first and second images. The output image shows the portion of the body and in the output image, artefacts which are generated by the anti-scatter arrangement, are reduced, suppressed or eliminated compared to the first and the second image.

Embodiments of the present disclosure further pertain to a computer program element, which when executed on a processor unit, instructs the processor to perform the steps of the method described in the previous paragraph.

DETAILED DESCRIPTION OF EMBODIMENTS

Figure 1:
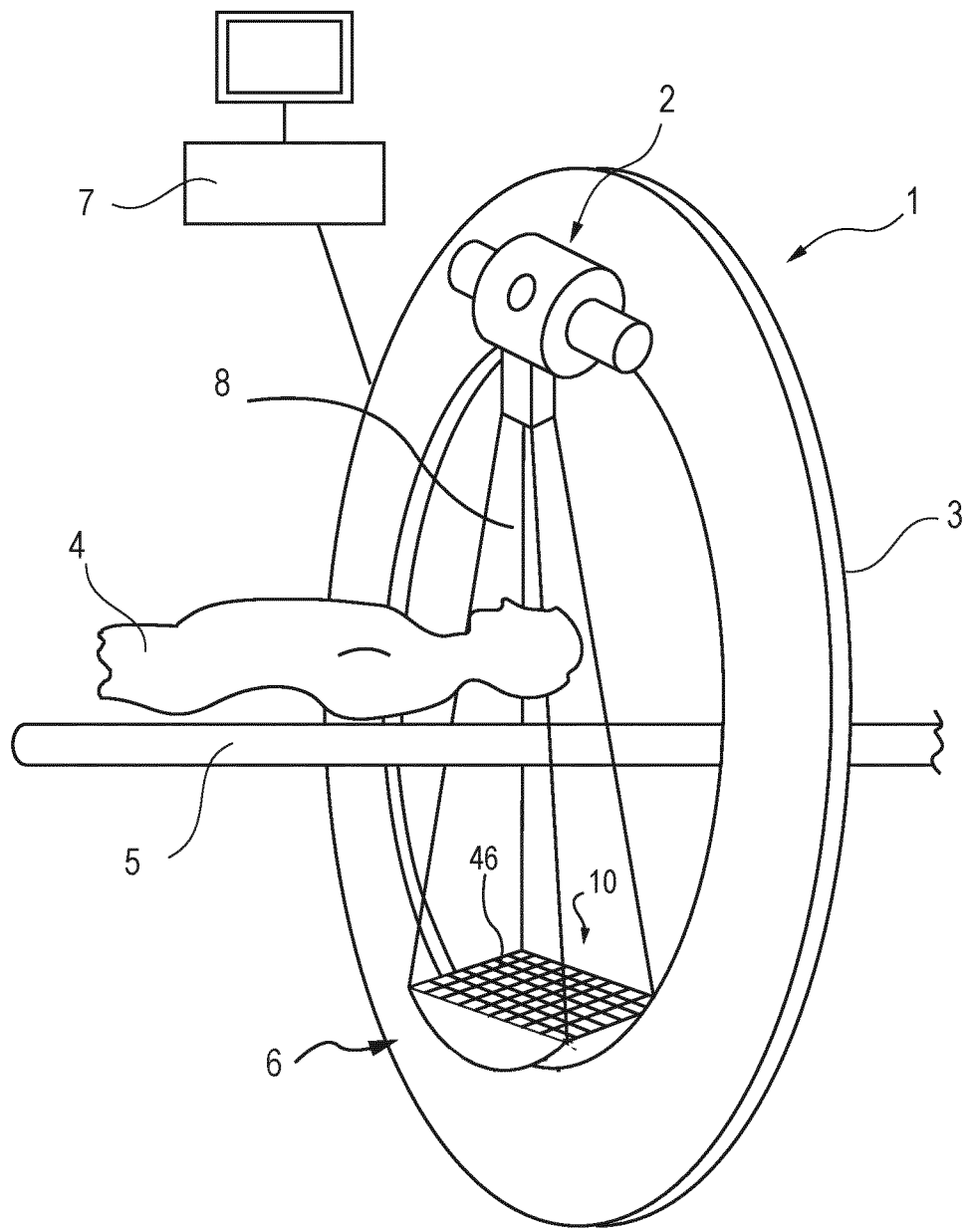
FIG. 1 is a schematic illustration of an X-ray imaging system according to a first exemplary embodiment.

FIG. 1 is a schematic illustration of an X-ray imaging system 1 according to a first exemplary embodiment. In the illustrated exemplary embodiment, the x-ray imaging system 1 is a fan beam computed tomography (FBCT) system configured as a multi-slice scanner. However, the present disclosure is not limited to such systems. By way of example, it is also possible to use the present disclosure with cone beam computed tomography systems (CBCT) and image guided therapy (IGT) systems. Further, the present disclosure can also be used in projection radiography systems.

As can be seen from FIG. 1, the X-ray imaging system 1 includes a gantry 3 on which an X-ray source 2 is mounted. The X-ray source 2 rotates with the gantry 3 as at the subject 4 moves on a patient support 5 through an opening formed by the gantry 3.

During rotation, the X-ray source produces a narrow, fan-shaped beam of X-rays that is emitted from an X-ray emitting region, which substantially represents a point source. It is conceivable that the X-ray source generates more than one X-ray emitting region, e.g. using multiple electron beams.

The fan-shaped beam passes through a section of the body of the subject 4. X-rays, which have passed through the body of the subject 4, are recorded by a detector system 6, which includes a two-dimensional array 46 of X-ray sensitive pixels, which form an X-ray sensitive surface 10.

As the X-rays interact with tissue within the subject's body, the X-rays become attenuated as well as scattered by the tissue. X-rays propagating in a direct line from the x-ray emitting region (i.e. the point source) to the detector system 6 are desired. On the other hand, contrast and signal-to-noise ratio of images acquired by the detector system 6 are reduced by tissue scatter. In order to reduce the influence of tissue scatter, the detector system 6 includes an anti-scatter arrangement (not shown in FIG. 1), which is arranged in the beam path of the X-rays between the subject 4 and the X-ray sensitive surface.

Figure 2:
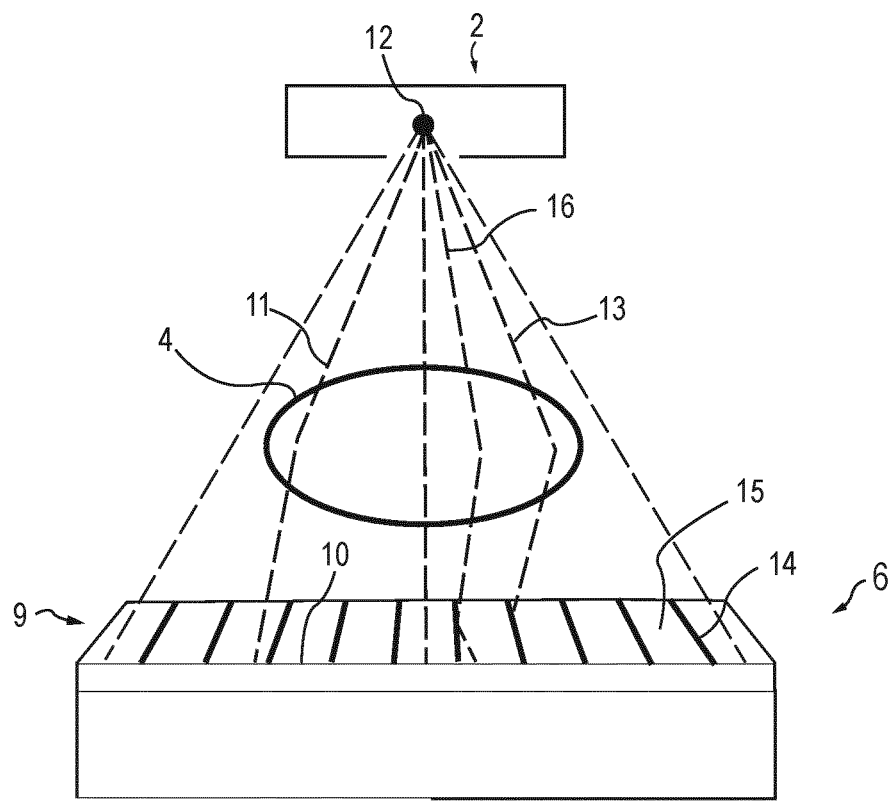
FIG. 2 is a further schematic illustration of the X-ray source, the detector system and the data processing system of the X-ray imaging system, which is shown in FIG. 1.

FIG. 2 is a schematic illustration which explains the structure and functioning of an exemplary anti-scatter arrangement 9. In the schematic illustration of FIG. 2, the detector system 6 has a flat X-ray sensitive surface 10. However, the present disclosure is also applicable to detector systems, which have a curved X-ray sensitive surface 10, which is curved in one or two dimensions. The X-ray sensitive surface 10 of the detector system 6 is formed from a plurality of pixels (not shown in FIG. 2), which are arranged in a two-dimensional array.

As can be further seen from FIG. 2, the anti-scatter arrangement 9 is arranged between the body of the subject 4 and the X-ray sensitive surface 10. The anti-scatter arrangement 9 includes a plurality of septa 14, which form a plurality of cells 15. The anti-scatter arrangement 9 may be configured as a linear (i.e. one-dimensional) or two-dimensional anti-scatter grid.

Compared to the cells 15, the septa 14 have a comparatively low X-ray transmittance so that X-rays, which are scattered within the body of the subject 4 at a sufficiently high angle (such as the X-ray designated with reference numeral 13), do not reach the X-ray sensitive surface 10, but are absorbed by the septa 14. On the other hand, unscattered X-rays, or X-rays, which are scattered at small angles (such as the X-ray 11) pass through the X-ray transmissive cells 15 and reach the X-ray sensitive surface 10 of the detector system 6.

The septa 14, which are shown in the exemplary embodiment of FIG. 2, form a focused anti-scatter grid, i.e. the grid cells 15, which are formed by the septa 14, point to the X-ray emitting region 12. Thereby, the anti-scatter arrangement 9 is focused in two dimensions. However, it is also conceivable that the anti-scatter arrangement is focused only in one dimension so that the grid cells 15 point to an axis, which substantially extends through the X-ray emitting region 12 (i.e. perpendicular to the paper plane of FIG. 2).

It is to be noted that the present disclosure is also applicable to unfocused anti-scatter grids, such as septa 14, which are oriented parallel to each other so that the cells point in a direction normal to the X-ray sensitive surface.

As can also be seen from FIG. 2, since the septa 14 have a comparatively low X-ray transmittance, they generate a shadow-like structure in the image acquired by the detector system 6. This has led to the development of filters for removing these artefacts. However, the filters, which have been developed in the prior art often lead to unsatisfactory results, which can constitute a limit for the diagnostic value of the images. This is of particular relevance if the anti-scatter arrangement 9 includes a two-dimensional anti-scatter grid, since the width of the septa of two-dimensional anti-scatter grids (i.e. measured in a direction parallel to the X-ray sensitive surface 10) is typically greater than the septa width of linear anti-scatter grids.

The reason for these satisfactory results is partly due to the fact that the artefact in the image is influenced by various different effects, such as residual scatter i.e. X-rays (such as the X-ray 16 in FIG. 2), which are scattered at one or more of the septa and still reach the X-ray sensitive surface 10. Further, these effects also include: deviations of the electron beam focal spot on the anode within the X-ray source 2 (which generates the X-ray emitting region 12), non-linear noise caused by preprocessing of the acquired image data, relative motion between the detector system 6 and the X-ray source 2 due to dynamic system distortions, beam hardening, non-linear, spectrum dependent low-frequency drop (LFD) at the septa 14, and memory effects, such as bright burn.

However, the inventors have found that it is possible to obtain X-ray images in which the artefacts, which are generated by the anti-scatter arrangement, are satisfactorily reduced, suppressed or even eliminated.

Figure 3:
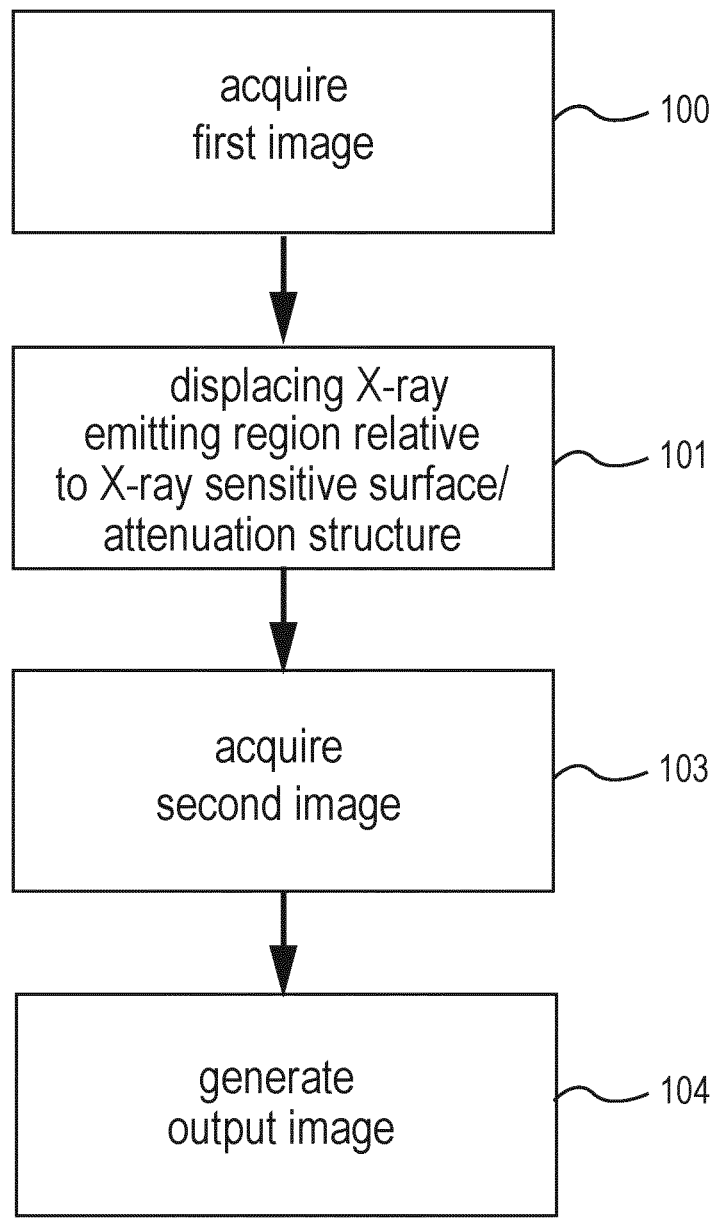
FIG. 3 is a flowchart of an exemplary method performed with the X-ray imaging system according to the first exemplary embodiment, which is shown in FIGS. 1 and 2.

FIG. 3 is a flow chart, which illustrates a method of determining artefact-free or substantially artefact-free images according to an exemplary embodiment using the X-ray imaging system 1 of the first exemplary embodiment, which is illustrated in FIGS. 1 and 2. After a first image is acquired (step 100), the X-ray emitting region, relative to a coordinate system, which is fixed relative to the anti-scatter arrangement and/or relative to a coordinate system, which is fixed relative to the X-ray sensitive surface, is brought to a new position (step 101) so that there is a relative displacement of the X-ray emitting region 12 relative to the anti-scatter arrangement 9 and/or the X-ray sensitive surface 10. This step is described in more detail in connection with FIGS. 4 to 5C. The displacement may be continuous and/or stepwise.

Then, a second image is acquired (step 103) so that at least a portion of the second image and the at least a portion of the first image show a same portion of the subject's body. The relative positions of the X-ray emitting region relative to the anti-scatter arrangement and/or the X-ray sensitive surface are so that the first and the second images are different from each other.

The inventors have acknowledged that the differences between the first and the second images allow generation of an output image (step 104), in which the artefacts, which appear in the first and second images, are reduced, suppressed or even eliminated. As is explained in more detail further below, in an exemplary embodiment, the algorithm for generating the output image includes a machine learning-based algorithm, such as an artificial neural network.

However, the invention is not limited to algorithms which use artificial neural networks. By way of example, generation of the output image may include determining a pixel-wise sum or a pixel-wise weighted sum of the input images. The data processing system may perform a matching operation for matching at least a portion of the first image with at least a portion of the second image before determining the sum or weighted sum. Thereby, pixel data values are combined, which correspond to a same or substantially same body portion of the subject.

According to a further embodiment, the generation of the output image is performed based on an algorithm which is disclosed in the article "Scene Segmentation Assisted by Stereo Vision", published in 2011 *International Conference* on *3D Imaging, Modeling, Processing, Visualization and Transmission*, pp. 57-64, doi: 10.1109/3DIMPVT.2011.16. The contents of this document is incorporated by reference for all purposes. A further algorithm based on which the output image can be generated is disclosed in the article "Stereoscopic Inpainting: Joint color and depth completion from stereo images," published in 2008 IEEE Conference on Computer Vision and Pattern Recognition, Anchorage, AK, 2008, pp. 1-8, doi: 10.1109/CVPR.2008.4587704. The contents of this document is incorporated by reference for all purposes.

According to a still further embodiment, the data processing is configured to use a trained artificial neural network for determining the output image. This embodiment is discussed in more detail further below in connection with FIGS. 6 to 7B.

Figure 4:
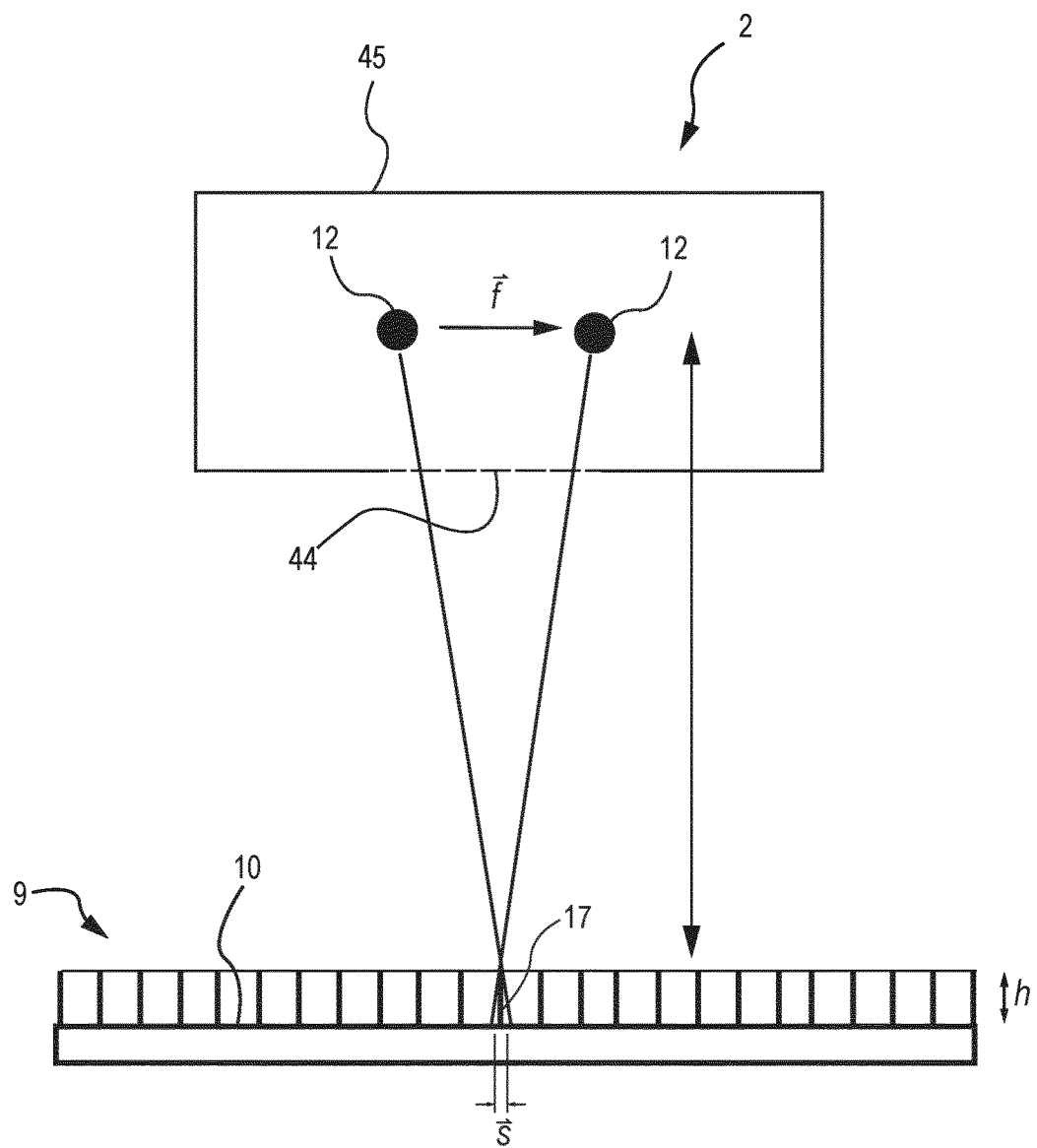
FIG. 4 is a schematic illustration of the imaging process for acquiring the first and second images in the exemplary method illustrated in FIG. 4, wherein the imaging process is performed using the X-ray imaging system according to the first exemplary embodiment, which is schematically illustrated in FIGS. 1 and 2.

FIG. 4 is a schematic illustration of how step 103 is performed by the X-ray imaging system according to the first exemplary embodiment (illustrated in FIGS. 1 and 2). For simplicity of of illustration, the anti-scatter arrangement 9 is not illustrated as a focused anti-scatter arrangement, as it is shown in FIG. 2. The X-ray imaging system is configured to displace the X-ray emitting region 12 within a housing 45 of the X-ray source 2 so that, relative to a coordinate system, which is fixed relative to the anti-scatter arrangement 9 and the X-ray sensitive surface 10, the position of the X-ray emitting region 12 is displaced. X-rays, which are emitted from the X-ray emitting region 12, exit from the housing 45 through an X-ray transmissive window 44, which has a higher X-ray transmittance compared to the walls of the housing 45.

As can be seen from FIG. 4, if the X-ray emitting region 12 is displaced within the housing 45 of the X-ray source (schematically illustrated by vector $\vec{f}$), the central projection of septum 17 (with the X-ray emitting region 12 being at the projection center), is shifted by a vector $\vec{s}$. Therefore, artefacts, which are generated by the anti-scatter arrangement 9, are different in the first and the second images. By way of example, the displacement of the X-ray emitting region 12 is performed by deflecting the electron beam, generated by the X-ray source 2 within the housing 45 so that the focal spot position within the housing 45 is displaced. The walls of the housing 45 are substantially radiopaque to that the X-rays are absorbed within the walls of the housing 45. A portion of the X-rays, which are generated within the X-ray emitting region 12, exit from the housing 45 through an X-ray transmissive window 44.

The X-ray source 2 may be configured to deflect the electron beam within the housing 45 using electrostatic and/or electromagnetic electron optical elements. This allows acquisition of the first and the second images within a time period of less than 20 milliseconds, or less than 200 microseconds.

Figure 5A:
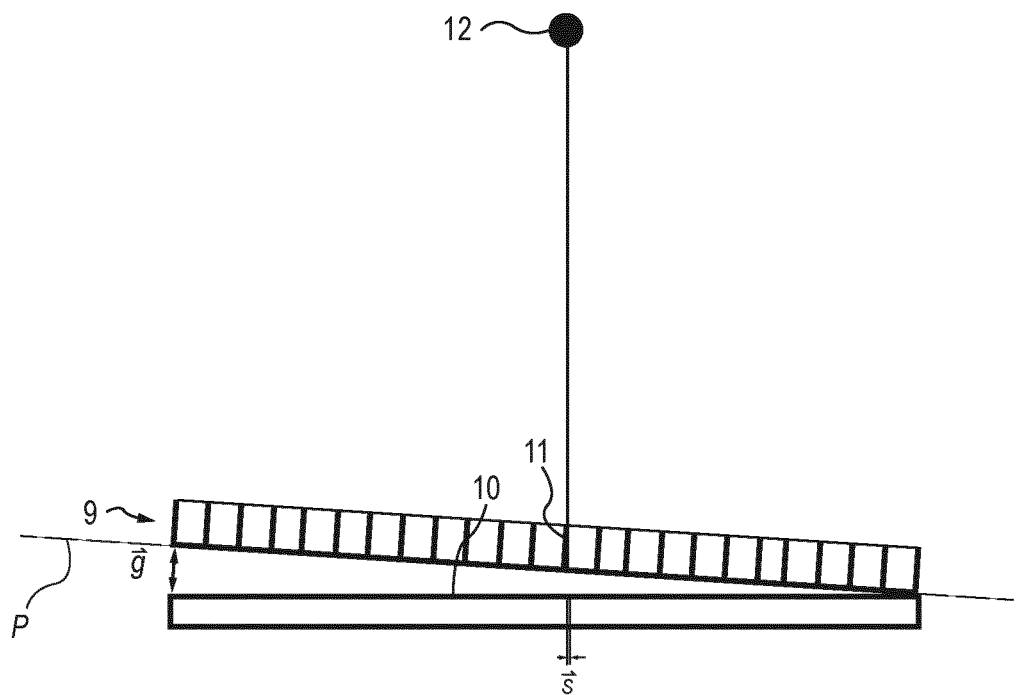
FIG. 5A is a schematic illustration of an imaging process for acquiring the first and the second images, wherein the imaging process is performed using an X-ray imaging system according to a second exemplary embodiment.
Figure 5B:
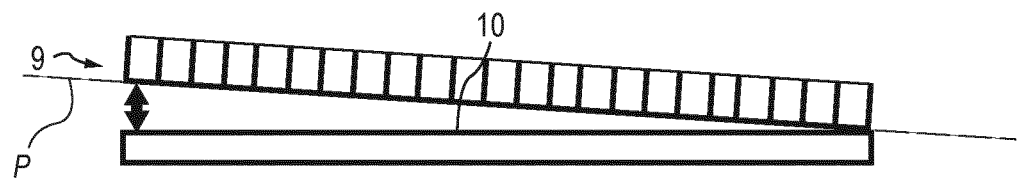
FIGS. 5B and 5C are a schematic illustrations of an imaging process for acquiring the first and the second images, wherein the imaging process is performed using an X-ray imaging system according to a third exemplary embodiment.
Figure 5C:
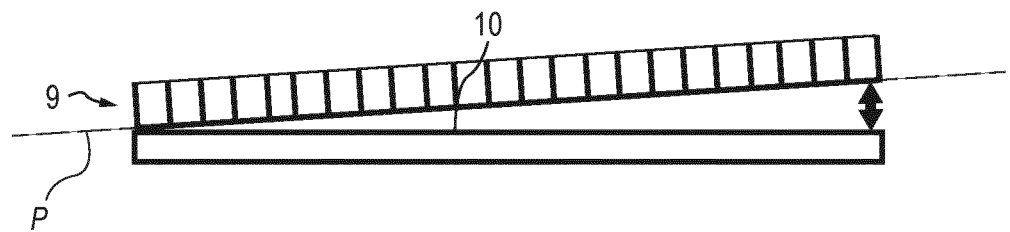

FIGS. 5A to 5C are schematic illustrations of how step 103 (shown in FIG. 3) is performed in an X-ray imaging system according to a second exemplary embodiment. The X-ray imaging system according to the second exemplary embodiment includes the same components, as have been explained in connection with FIGS. 1 and 2 for the first exemplary embodiment. Specifically, similarly to the X-ray imaging system according to the first exemplary embodiment, the anti-scatter arrangement of the second exemplary embodiment can be a focused or unfocused anti-scatter arrangement.

The X-ray imaging system according to the second exemplary embodiment is configured so that an orientation between the anti-scatter arrangement 9 and the X-ray receiving surface 10 is varied so that the first and the second images are acquired at different orientations. In this embodiment, the X-ray sensitive surface 10 and the light emitting region 12 remain stationary relative to a space-fixed coordinate system. However, it is also conceivable that, relative to the space-fixed coordinate system, in addition to the movement of the anti-scatter arrangement 9, also the X-ray sensitive surface 10 and/or the light emitting region 12 are displaced. The X-ray imaging system may include an actuator, which is in operational communication with the anti-scatter arrangement 9. The X-ray imaging system may be configured so that variation of the orientation of the anti-scatter arrangement 9 relative to the X-ray sensitive surface 10 includes controlling the actuator. By way of example, the actuator may include a piezo element.

Specifically, as is shown in FIG. 5A in the second exemplary embodiment, a displacement (schematically illustrated by vector $\vec{g}$) of the anti-scatter arrangement 9 at a first end and a non-displacement of the anti-scatter arrangement 9 at a second end, which is opposed to the first end, has the effect that, in a coordinate system, which is stationary relative to the anti-scatter arrangement 9, the X-ray emitting surface 12 is displaced relative to the anti-scatter arrangement 9. The displacement of the anti-scatter arrangement 9 has the effect that a major plane P of the anti-scatter arrangement 9 is moved from a parallel orientation relative to the X-ray sensitive surface 10 (not illustrated) to an angled orientation relative to the X ray sensitive surface 10 (illustrated in FIG. 5A). As can be seen from FIG. 5A, the displacement has the effect that the central projection of the septum 11 onto the X-ray sensitive surface 10 (with the X-ray emitting region 12 being at the projection center), is shifted (schematically illustrated by vector $\vec{s}$).

In the second exemplary embodiment, the X-ray imaging system is configured to image a first of the two images, when the major plane P of the anti-scatter arrangement 9 is arranged parallel relative to the X-ray sensitive surface 10 of the detector system 9 and a second one of the two images is acquired in the configuration, which is shown in FIG. 5A, i.e. when the major plane P of the anti-scatter arrangement 9 is angled relative to the X-ray sensitive surface 10.

On the other hand, in an alternative embodiment, which is shown in FIGS. 5B and 5C, the anti-scatter arrangement 9 is moved between two angled orientations relative to the X-ray sensitive surface 10 for acquiring a first one of the two images in the orientation, which is shown in FIG. 5B and the second one of the two images in the orientation, which is shown in FIG. 5C. By way of example, the orientation angles of the two angled orientations are of opposite sign and of equal or unequal magnitude. It has been shown that the increase in the difference between the first and the second image, compared to the embodiment described in connection with FIG. 5, causes an improved reduction or suppression of the image artefacts associated with the anti-scatter arrangement 9. Specifically, the inventors have shown through calculations that this yields a larger effective signal, which results in an improved performance.

However, it is also conceivable that the orientation angles of the two angled orientations have the same sign.

In a further alternative embodiment, which is not shown in the Figs., the anti-scatter arrangement 9 is displaced relative to the X-ray sensitive surface 10 by a translatory movement. By way of example, the anti-scatter arrangement 9 maybe displaced relative to the X-ray sensitive surface 10 in a direction parallel to the X-ray sensitive surface 10.

It is further conceivable that two components of the group consisting of the X-ray emitting surface 12, the anti-scatter arrangement 9 and the X-ray sensitive surface 10 are moved and the remaining one of these components remains stationary.

Figure 6:
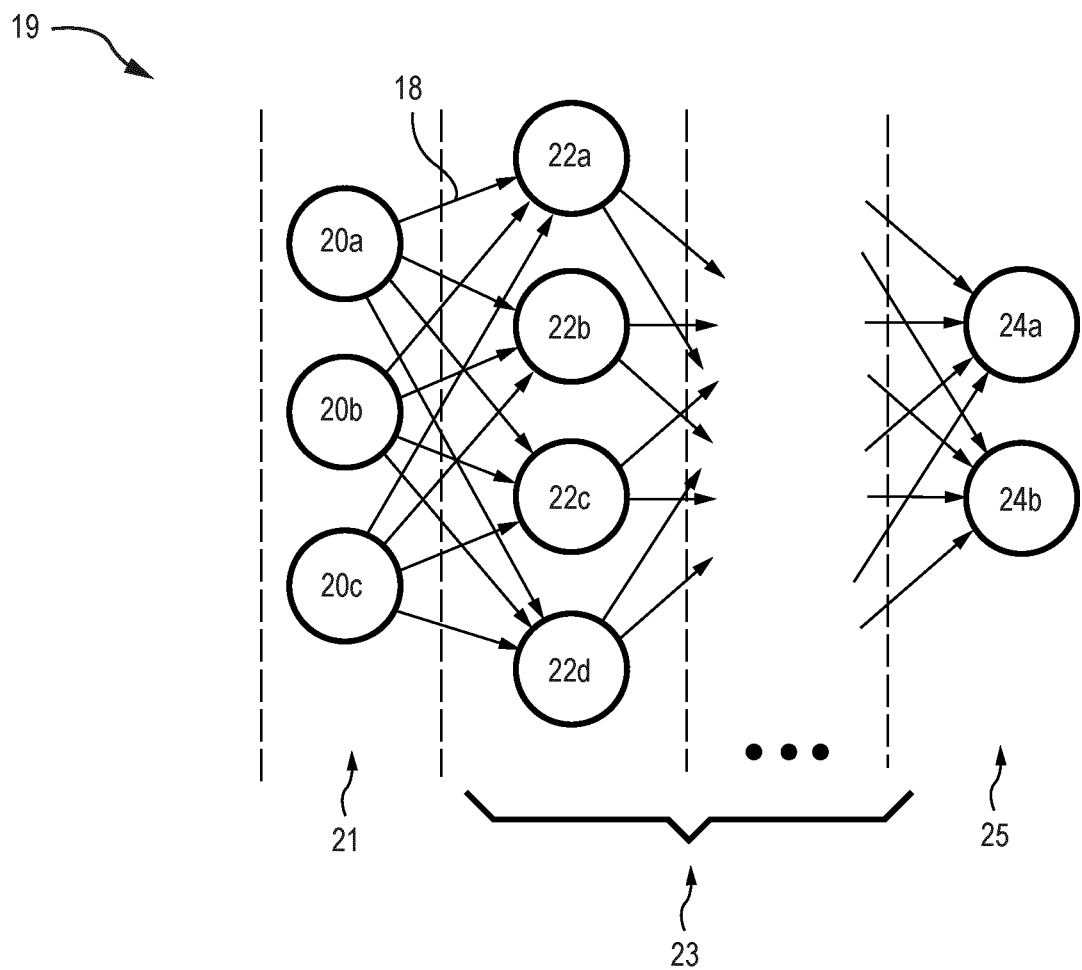
FIGS. 6, 7A and 7B are a schematic illustrations of an artificial neural network used for processing the first and the second images in an the X-ray imaging system, according to any one of the exemplary embodiments.

FIG. 6 is a schematic illustration of an artificial neural network (ANN) 19, which may be used to determine the output image based on the first and second images using the data processing system, which is designated in FIG. 1 with reference numeral 7. Exemplary methods for training the ANN are described in more detail further below.

As can be seen from FIG. 6, the ANN 19 includes a plurality of neural processing units 20a, 20b, . . . 24b. The neural processing units 20a, 20b, . . . 24b are connected to form a network via a plurality of connections 18 each having a connection weight. Each of the connections 18 connects a neural processing unit of a first layer of the ANN 19 to a neural processing unit of a second layer of the ANN 19, which immediately succeeds or precedes the first layer. Thereby, the artificial neural network has a layer structure which includes an input layer 21, at least one intermediate layer 23 (also denoted as hidden layer) and an output layer 25. In FIG. 4a, only one of the intermediate layers 23 is schematically illustrated. The ANN 19 may include more than 5, or more than 10 intermediate layers. The number of layers of the ANN 19 may be less than 7, or less than 15.

Figure 7A:
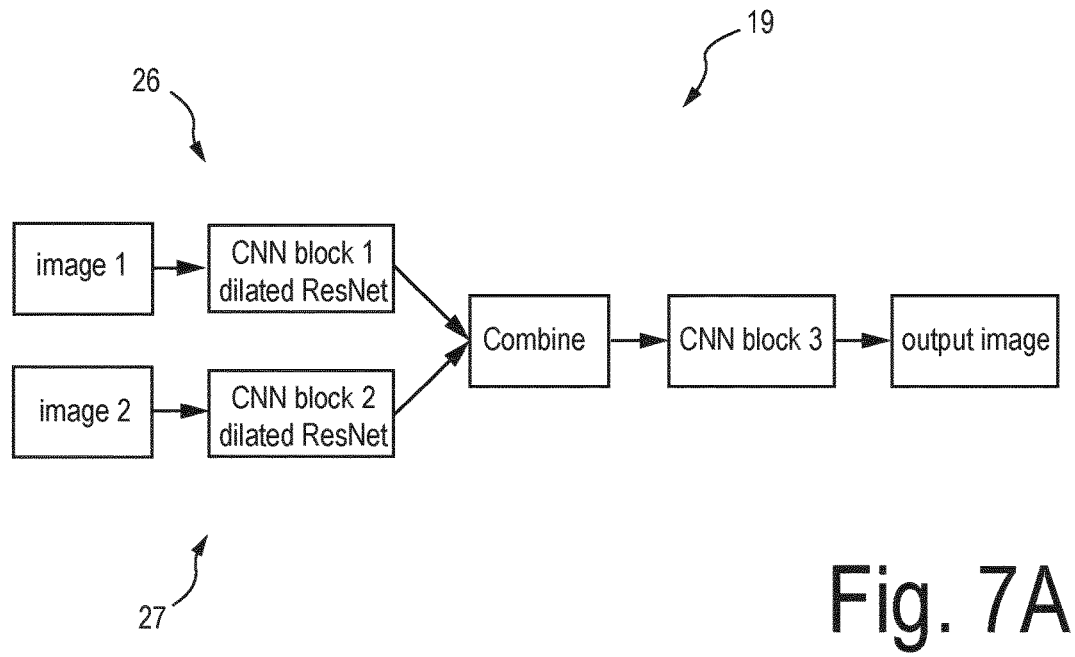
Figure 7B:
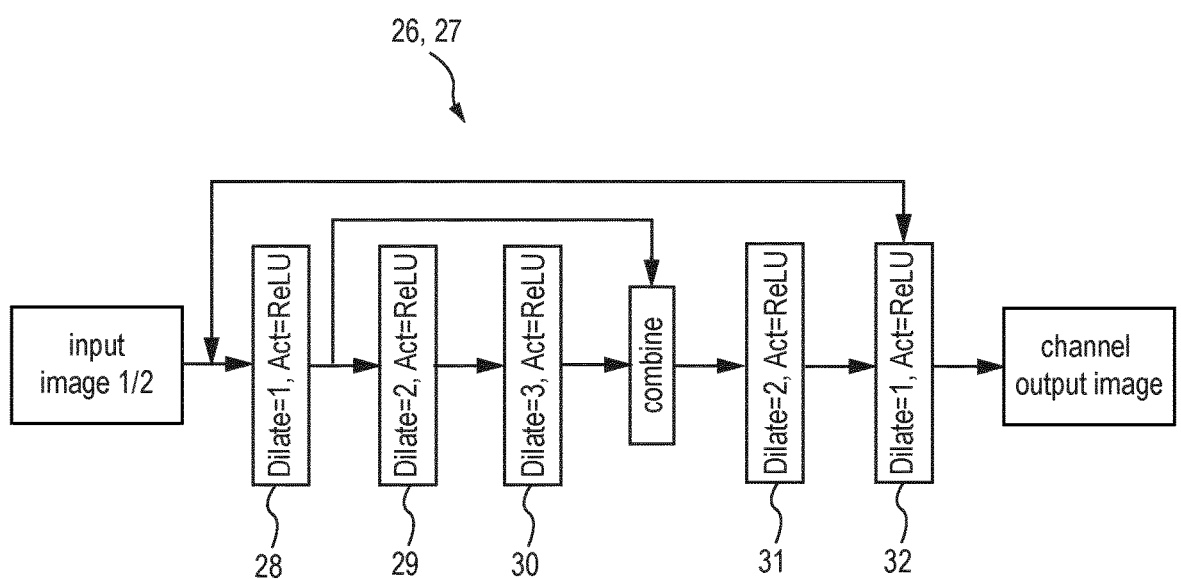

FIGS. 7A and 7B are further schematic illustrations of aspects of the ANN 19. As can be seen in FIG. 7A, the ANN 19 has two image input channels 26, 27. The first input channel 26 is configured to receive at least a portion of the first image and the second input channel 27 is configured to receive at least a portion of the second input image. In the illustrated exemplary embodiment, the layer structure of the input channels 26, 27 is identical. However, it is conceivable that the input channels 26, 27 have different layer structures.

Each of the input channels 26, 27 generates a channel output image. Each of the input channels includes an ANN, which may be configured as a convolutional neural network (CNN). An example of a CNN, which can be used in one or both input channels 26, 27 is discussed in more detail below in connection with FIG. 7B. It is also conceivable that one or both of the input channels are non-machine learning algorithms.

The channel output images of the two input channels 26, 27 are combined and the combined image is an input for an ANN, which may be configured as a CNN. This ANN generates the output image or an image based on which the output image is generated. Combining the channel output images may include pixel-wise adding the channel output images or forming a weighted sum. However, further or and/or additional operations are conceivable for combining the images. By way of example, in alternative embodiments, the combining operation may include one or a combination of: pixel-wise multiplication, pixel-wise subtraction or pixel-wise division.

As can further be seen from FIG. 7A, at least one of the input channels 26, 27 may include or may consist of a residual network, in particular a dilated residual network. The residual network may include layers having a non-linear activation function, such as a Rectified Linear Unit (ReLU) activation function. The residual connection may be used to combine output data of different layers. Combining the output data may include forming a sum or a weighted sum of the output data of the layers. Additionally or alternatively, combining the output data may include one or a combination of: pixel-wise subtraction, pixel-wise division, pixel-wise multiplication.

FIG. 7B is an exemplary embodiment of a dilated residual network, which can be used for implementing the first input channel 26 and/or the second input channel 27. As can be seen from FIG. 7B, the input channel includes five directly consecutive dilated convolutional layers. Each of the layers has a Rectified Linear Unit activation function. A first layer 28, which receives the input image, has a dilation factor of 1. A second layer 29, which receives output from the first layer 28, has a dilation factor of 2. A third layer 30, which receives output from the second layer 29 has a dilation factor of 3. A fourth layer 31, which receives combined data, which is generated based on the output of the third layer 30 and the input image, has a dilation factor of 2. In other words, the fourth layer 31 receives data of the input image through a residual connection. By way of example, generating the combined data may include generating a pixel-wise sum or a pixel-wise weighted sum based on the input image and the output of the third layer 30. Additionally or alternatively the generation of the combined data may include Additionally or alternatively, combining the output data may include one or a combination of: pixel-wise subtraction, pixel-wise division, pixel-wise multiplication.

The ANN may be trained based on images, which have been acquired without an anti-scatter arrangement in the beam paths of the X-rays. The first and second images may then be calculated based on numerical simulations, which simulate, based on the artefact-free images, the artefact generated by the anti-scatter arrangement. Specifically, the artefact generated by the anti-scatter arrangement may be determined using ray-tracing simulation techniques for each of the first and second images. Examples for simulating artefacts generated by the anti-scatter arrangement are given in the article "Acuros CTS: A fast, linear Boltzmann transport equation solver for computed tomography scatter—Part I: Core algorithms and validation", written by Alexander Maslowski et al. and published in Med. Phys. 45 (5), (2018), pages 1899 to 1913, the contents of this document is incorporated by reference for all purposes.

It is also conceivable that the ANN is trained based on first and second images, which have been acquired with an anti-scatter arrangement in the beam path of the X-rays, and further based on a third image, acquired from substantially the same body portion as the first and second images, but without an anti-scatter arrangement in the beam path of the X-rays.

Figure 8A:
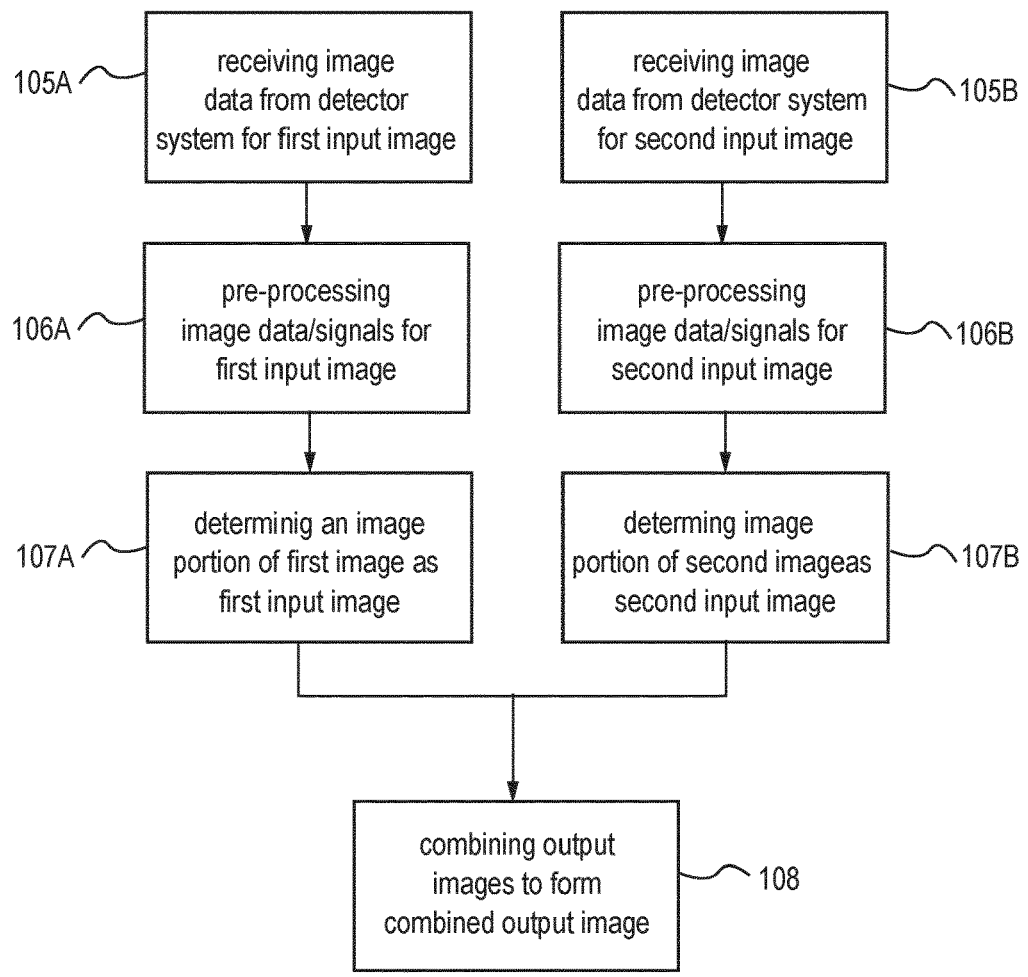
FIGS. 8A and 8B schematically illustrate the process for processing the first and the second images using the artificial neural network, which is schematically illustrated in FIGS. 6, 7A and 7B.
Figure 8B:
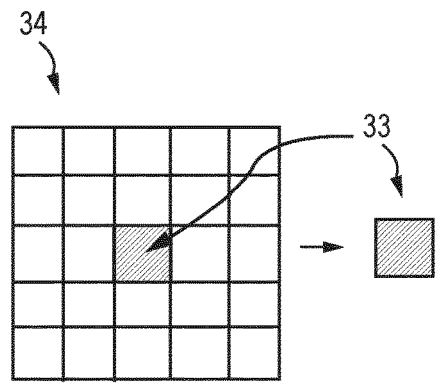

FIGS. 8A and 8B are schematic illustration of how the images, which have been acquired by the detector, are processed for forming the input images based on which the output images are generated by the data processing system. The data processing system receives image data representing the first and second images from the detector system (steps 105A, 105B). It is conceivable, that the detector system is configured to preprocess the data before transmitting the data to the data processing system. Examples for such preprocessing routines are, but are not limited to: detector gain correction, offset correction and defect correction. Typically such preprocessing routines are implemented within the detector. The image data of the first and second images are acquired in a time consecutive manner so that the images represent different relative positions of the one or more X-ray emitting regions relative to the anti-scatter arrangement and/or relative to the X-ray sensitive surface (measured relative to a coordinate system, which is stationary relative to the anti-scatter arrangement and/or stationary relative to the X-ray sensitive surface).

For each of the received first and/or second images, the data processing system may perform preprocessing of the image data (steps 106A and 106B). The preprocessing may include but is not limited to one or a combination of: defect correction, gain correction and offset correction. However, it has been shown by the inventors that a sufficient reduction, suppression or elimination of image artefacts generated with the anti-scatter arrangement can be obtained, even without preprocessing the image data by the detector system and/or the data processing system.

The data processing system determines (steps 107A and 107B), for each of the first and second images, an image portion, which serves as the input image for the algorithm for determining a corresponding output image in which the artefacts associated with the anti-scatter arrangement are reduced, suppressed or eliminated. The image portion, which is determined by the data processing system in steps 107A and 107B, may be a non-divided image portion. By way of example, the image portion may be a two-dimensional array of adjacent pixels having a square or rectangular configuration. FIG. 8B schematically illustrates an example of such an image portion 33, which is determined from the first image 34.

In the steps 107A and 107B, the determined image portions may be image portions, which show the same or substantially the same body portion of the imaged subject.

By way of example, the image portion has a size of X times Y pixels, wherein X and Y (which need not to be of the same size) are within the range of between 50 and 250. Each of the image portions may show artefacts associated with the anti-scatter arrangement. Specifically, in the event that the anti-scatter arrangement includes a linear (i.e. one-dimensional) or a two-dimensional anti-scatter grid, the image portion may show, in each of the grid directions between 1 and 10 artefact structures, each of which associated with one of the septa of the anti-scatter grit. The term "grid direction" may be defined to mean a direction perpendicular to a longitudinal axis of at least one of the grid septa, which form the linear or two-dimensional anti-scatter grid.

Each of the first and second images may have a size of N times M pixels, wherein N and M (which need not to be of the same size) may be within the range of between 250 and 4,000. It has been shown by the inventors that dividing the first and the second images received from the detector system into portions and processing pairs of image portions, which show or substantially show the same body portion of the subject can increase processing speed so that the combined output image, which is composed of the individual output images which relate to the input image portions, can be obtained within a shorter period of time. A further advantage is that such a technique has lower memory requirements. Further, training processes, which use image regions may make it easier to generate the output image.

The ANN may be configured as a fully convolutional network and the size of the image regions may be equal to or greater than twice the receptive field of the convolutional neural network.

By way of example, the receptive field of the convolutional neural network may be in a range of between 10 and 30. Therefore, values for X and Y, which characterize the size of the image regions may be equal to or greater than 50 or equal to or greater than 100.

It is to be noted that the process of determining image portions, which is illustrated in FIGS. 8A and 8B, can be used in any one of the above described (machine learning based on non-machine learning based) methods for determining the output image based on the two input images.

FIGS. 9A to 11 are schematic illustrations of components of an X-ray imaging system according to a third exemplary embodiment. The third exemplary embodiment the same components as have been described for the first exemplary embodiment in connection with FIGS. 1 and 2.

According to the third exemplary embodiment, the X-ray imaging system includes a position measuring unit, which is configured to acquire position data, which are indicative of a position of the one or more X-ray emitting regions during acquisition of the first and/or second image. Specifically, the X-ray imaging system may be configured to determine the position data separately for each of the first and second images or to acquire common position data for the first and the second images.

Examples for such position measuring units are described below in detail in connection with FIGS. 9A to 11. The data processing system of the third exemplary embodiment is configured to determine the output image based on the first image, the second image and the position data. By way of example, each of the first and second input channels may be configured to receive, in addition to the image data values of the first and second images, the position data of the respective image or data, which are determined based on the position data.

For each of the first and second images, the position data, or the data which are determined based on the position data, may be appended to the image data of the respective image.

By way of example, the ANN may be configured as conditional convolutional neural network. For each of the first and second images, the position data may be appended to the respective image using a one-hot vector. The size of the one-hot vector may correspond to the number of positions of the X-ray emitting regions used during training.

For algorithms, which are not based on artificial neural networks, the position data may be used to determine the distance between the X-ray emitting regions. Thereby, an higher accuracy in reducing, suppressing or eliminating the artefacts generated by the anit-scatter arrangement can be obtained, since the distance between the X-ray emitting regions is determined with a higher accuracy.

It has been shown by the inventors that using the position data for determining the output image leads to an improved reduction, suppression or elimination of the artefacts which are generated by the anti-scatter arrangement.

It is to be noted that the third exemplary embodiment can be used in combination with any one of the techniques, which are described herein for generating a relative displacement of one or more X-ray emitting regions relative to the anti-scatter arrangement and/or relative to the X-ray sensitive surface, measured in a coordinate system, which is stationary relative to the anti-scatter arrangement and/or stationary relative to the X-ray sensitive surface.

Figure 9A:
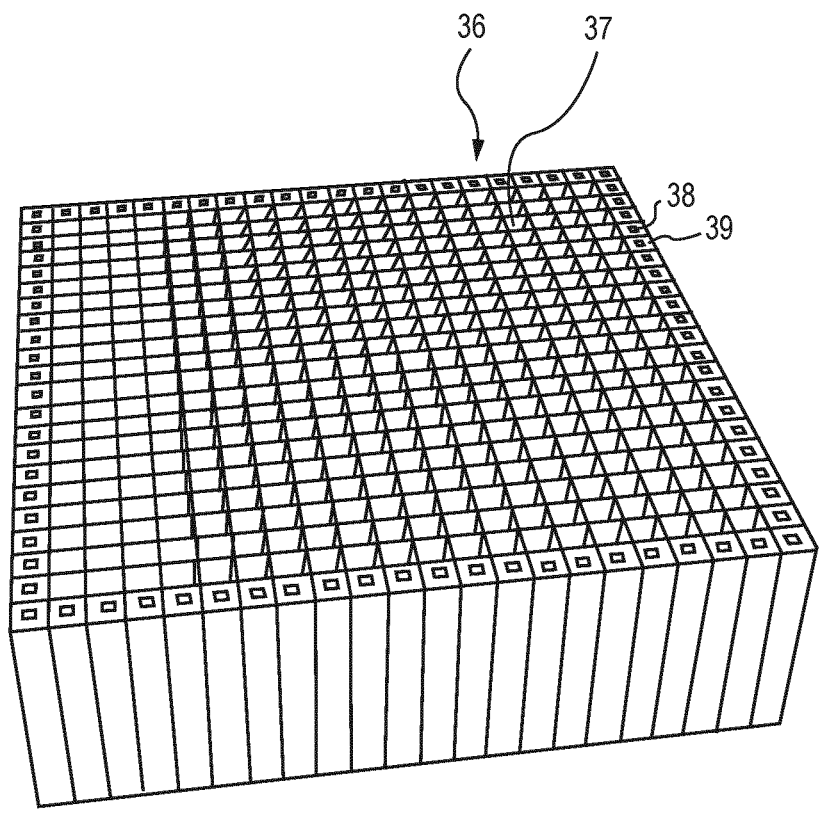
FIGS. 9A and 9B are schematic illustrations of a position measurement unit for measuring the location of an X-ray emitting region of an X-ray imaging system according to a third exemplary embodiment.

FIG. 9A is a schematic illustration of the anti-scatter arrangement 9, of the X-ray imaging system according to the third exemplary embodiment. The anti-scatter arrangement 9 is configured as a two-dimensional anti-scatter grid 37 having a crossed-grid structure. However, it is also conceivable that the anti-scatter arrangement 9 is configured as a linear anti-scatter grid. As seen in a plane, which is parallel to the X-ray sensitive surface, the crossed-grid structure 37 is surrounded by a plurality of X-ray apertures, such as the X-ray aperture 38. It is to be noted that it is also conceivable that the position measuring unit only includes one, or any number less than 5, or any number less than 10 X-ray apertures.

The X-ray aperture 38 has a comparatively high x-ray transmittance compared to material, which surrounds the X-ray aperture 38. By way of example, the X-ray aperture 38 is a hole formed in a metal part 39. The metal part 39 may contain or may include as a main constituent one or a combination of: tungsten (W), lead (Pb) or tantalum (Ta).

Figure 9B:
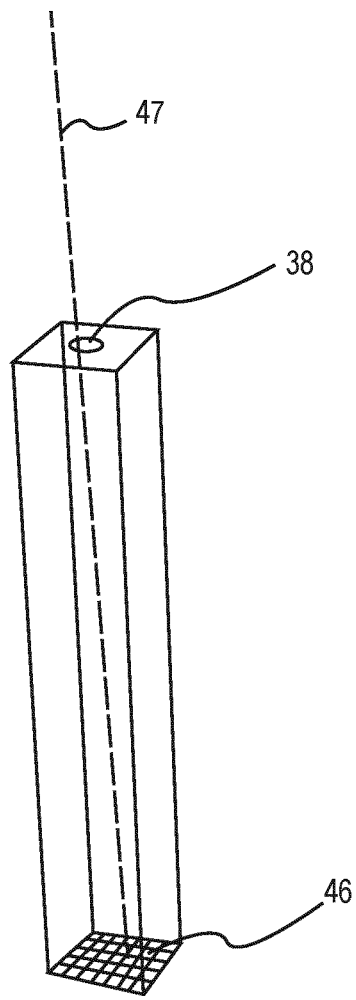

FIG. 9B schematically illustrates the functioning of the positioning measuring unit. X-rays (such as the X-ray 47), which have passed through the X-ray aperture 38 form a pattern 40 on an X-ray sensitive surface 41 of the position measuring unit. The X-ray sensitive surface 41 may be formed by an array of X-ray sensitive pixels. Additionally or alternatively, the X-ray sensitive surface 41 may be part of the X-ray sensitive surface 10 (shown in FIG. 2). The data processing system may be configured to determine, based on the detected pattern, measurements data, which are indicative of the position of the one or more X-ray emitting regions, which are generated by the X-ray source.

Figure 10:
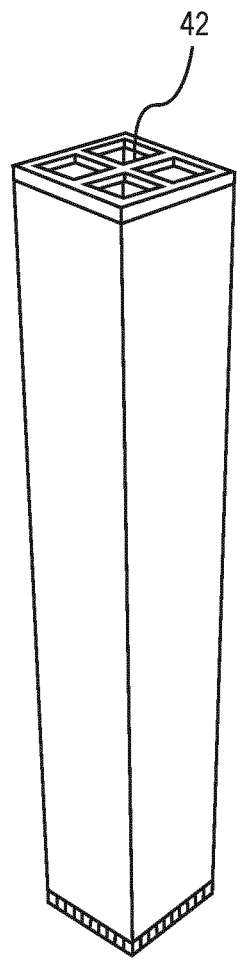
FIG. 10 is a schematic illustration of an alternative embodiment of a position measurement unit for measuring the location of an X-ray emitting region in the X-ray imaging system according to the third exemplary embodiment.

It is conceivable that, additionally or alternatively to the X-ray apertures, which are illustrated in FIG. 9A and 9B, other structures of a material of comparatively high X-ray transmittance can be used for generating a pattern on the X-rays sensitive surface. By way of of example, as is shown in FIG. 10, the structure may be in the form of a crosshair 42.

Figure 11:
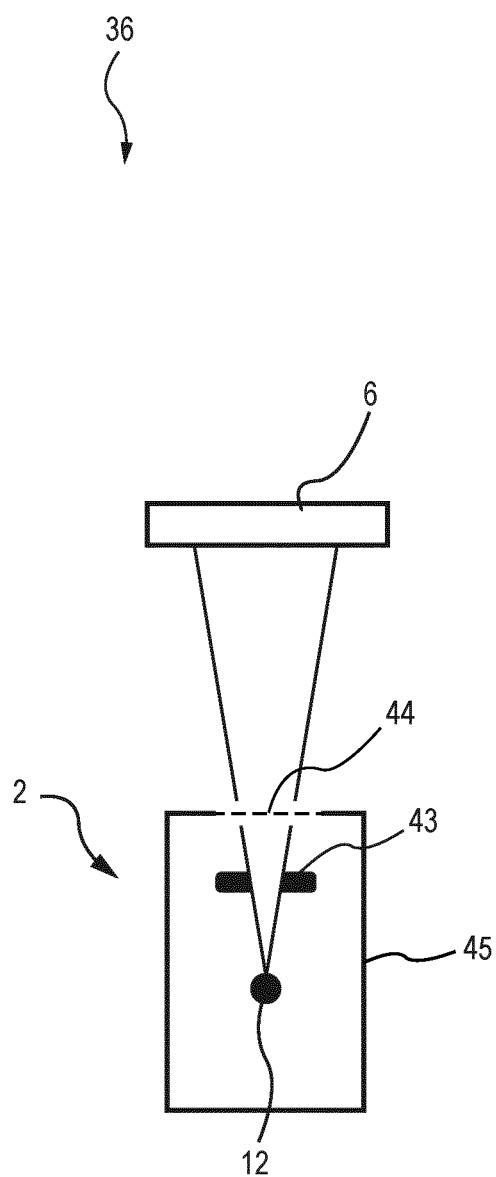
FIG. 11 is a schematic illustration of a still further alternative embodiment of a position measuring system of an X-ray imaging system according to the third exemplary embodiment.

FIG. 11 schematically illustrates a further exemplary embodiment of a position measuring unit, which includes a structure 43, which is arranged with in the X-ray source, and which has a lower X-ray transmittance compared to the X-ray transmissive window 44 through which the X-rays exit from the housing 45 of the X-ray source 2. Thereby, the structure 43 generates a pattern in the image, which is indicative of the position of the one or more X-ray emitting regions 12.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the protective scope of the claims of the present invention. In the claims, the word "comprising" does not exclude other elements or steps, and the indefinite article "a" or "an" does not exclude a plurality. Any reference signs in the claims should not be construed as limiting the scope.

The invention claimed is:

1. An X-ray imaging system for acquiring two-dimensional or three-dimensional images of a subject, the imaging system comprising:
    an X-ray source configured to emit X-rays from one or more X-ray emitting regions;
    a detector system configured to receive a portion of the X-rays, which has been passed through the subject, wherein the X-rays are received on an X-ray sensitive surface of the detector system;
    an anti-scatter arrangement, which is arranged in the beam path of the X-rays between the X-ray emitting region and the detector system;
    wherein the imaging system is configured to acquire a first and a second image of the subject, wherein each of the first and second images shows
        (a) a same portion of a body of the subject and
        (b) an image artifact generated by the anti-scatter arrangement (9);
    wherein the imaging system is configured to:
    control a relative position of at least one of the one or more X-ray emitting regions, as seen in a coordinate system which is stationary relative to the anti-scatter arrangement and/or the X-ray sensitive surface so that the first and second images are acquired at different relative positions of the at least one X-ray emitting region relative to the anti-scatter arrangement and/or the X-ray sensitive surface; and to
    generate, using a data processing system of the imaging system, an output image, based on each of the first and second images;
    wherein the output image shows the portion of the body and in the output image, artefacts generated by the anti-scatter arrangement, are reduced, suppressed or eliminated compared to the first and the second image.

2. The imaging system of claim 1, wherein the data processing system is configured to use an algorithm, which uses differences between the first and the second images, which are caused by the different relative positions of the at least one X-ray emitting region to obtain the reduction, suppression, or elimination of the artefacts associated with the anti-scatter arrangement.

3. The imaging system of claim 1, wherein the data processing system is configured to generate the output image using a machine learning based algorithm;
    wherein the machine learning based algorithm generates the output image based on data of, or derived from, the first image and the second image.

4. The imaging system of claim 3, wherein the machine learning based algorithm comprises an artificial neural network (ANN).

5. The imaging system of claim 4, wherein the ANN has at least two image input channels,
    wherein the data processing system is configured to
    (a) use a first one of the image input channels for data of, or derived from at least a portion of the first image; and
    (b) use a second one of the image input channels for data of or derived from at least a portion of the second image.

6. The imaging system of claim 1, wherein the generation of the output image comprises:
    determining, using the data processing system, a plurality of image regions of the first image and a plurality of image regions of the second image, which substantially correspond to the image regions of the first image so that a plurality of pairs of substantially corresponding image regions are obtained;
    sequentially processing the pairs, using the data processing system, to generate, for each of the pairs, a corresponding region of the output image.

7. The imaging system of claim 1, wherein a distance between the different relative positions is at least 50 micrometers or at least 400 micrometers.

8. The imaging system of claim 1,
    wherein the anti-scatter arrangement comprises a one-dimensional or two-dimensional array of cells, which are separated from each other by septa;
    wherein an X-ray transmittance of each of the cells is greater than an X-ray transmittance of the septa.

9. The imaging system of claim 1, wherein the X-ray source comprises a housing which houses and electron optical system for generating one or more election beams and a target for receiving the one or more electrons beam so that the one or more X-ray emitting regions are arranged within the housing;
    wherein the imaging system is configured to control the X-ray source to controllably displace the at least one X-ray emitting region within the housing.

10. The imaging system of claim 9, wherein at least one of (a) and (b) holds true:
    (a) the electron optical system is configured to selectively deflect the electron beam so that an impingement location of the electron beam on the target is changed; wherein the control of the relative position of the at least one X-ray emitting region comprises varying the impingement location on the target using the electron optical system; and (b) the X-ray source is configured to generate a first electron beam generating a first X-ray emitting region and a second electron beam generating a second X-ray emitting region, wherein the control of the relative position of the at least one or more X-ray emitting regions comprises actuating and deactivating the two electron beams so that the electron beams are sequentially activated.

11. The imaging system of claim 1, further comprising an actuator, which is in operational communication with at least a portion of the anti-scatter arrangement and/or with at least a portion of the detector system;
    wherein the imaging system is configured so that the variation of the position of the at least one X-ray emitting region relative to the anti-scatter arrangement and/or relative to the X-ray sensitive surface comprises controlling the actuator.

12. The imaging system of claim 1, wherein the imaging system is configured to acquire the first and the second image within a time period of less than 20 milliseconds, or less than 200 microseconds.

13. The imaging system of claim 1, further comprising a measurement unit which is configured to acquire position data indicate of a position of one or more of the X-ray emitting regions.

14. The imaging system of claim 13, wherein the data processing system is configured to determine the output image further based on the position data.

15. A method for operating an X-ray imaging system for acquiring two-dimensional or three-dimensional images of a subject and for reducing artefacts which are generated by an anti-scatter arrangement of the X-ray imaging system;
    wherein the X-ray imaging system comprises:
        an X-ray source configured to emit X-rays from one or more X-ray emitting regions;
        a detector system configured to receive a portion of the emitted X-rays, which have been passed through the subject on an X-ray sensitive surface of the detector system;
    wherein the anti-scatter arrangement is arranged in the beam path of the X-rays between the subject and the detector system;
    wherein the method comprises:
    acquiring a first and a second image of the subject so that each of the first and second images shows at least a same portion of a body of the subject and (b) an artifact generated by the anti-scatter arrangement;
    controlling a relative position of at least one of the X-ray emitting regions relative to the anti-scatter arrangement and/or the X-ray sensitive surface so that the first and second images are acquired at different relative positions of the at least one X-ray emitting region; and
    generating, using a data processing system of the imaging system, an output image, based on each of the first and second images;
    wherein the output image shows the portion of the body and in the output image, artefacts which are generated by the anti-scatter arrangement, are reduced, suppressed or eliminated compared to the first and the second image.

16. Computer program element, which when executed on a processor unit, instructs the processor to perform the steps of the method according to claim 15.

* * * * *